United States Patent
Schena (10) Patent No.: US 10,631,713 B2
(45) Date of Patent: Apr. 28, 2020

(54) MULTI-STAGE INSTRUMENT CONNECTOR

(71) Applicant: Intuitive Surgical Operations, Inc., Sunnyvale, CA (US)

(72) Inventor: Bruce M. Schena, Menlo Park, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 200 days.

(21) Appl. No.: 15/262,653

(22) PCT Filed: Mar. 17, 2015

(86) PCT No.: PCT/US2015/020879
§ 371 (c)(1),
(2) Date: Sep. 12, 2016

(87) PCT Pub. No.: WO2015/142787
PCT Pub. Date: Sep. 24, 2015

(65) Prior Publication Data
US 2017/0181604 A1 Jun. 29, 2017

Related U.S. Application Data

(60) Provisional application No. 61/954,200, filed on Mar. 17, 2014.

(51) Int. Cl.
*A61B 1/00* (2006.01)
*A61B 34/00* (2016.01)
(Continued)

(52) U.S. Cl.
CPC ...... *A61B 1/00117* (2013.01); *A61B 1/00112* (2013.01); *A61B 1/00114* (2013.01);
(Continued)

(58) Field of Classification Search
CPC ............ A61B 1/00117; A61B 1/00124; A61B 1/00126; A61B 34/20; A61B 34/30;
(Continued)

(56) References Cited

U.S. PATENT DOCUMENTS 4,014,343 A * 3/1977 Esty ............... A61B 18/1402
219/233
4,524,761 A 6/1985 Hattori et al.
(Continued)

OTHER PUBLICATIONS

International Preliminary Report on Patentability for Application No. PCT/US15/20879, dated Sep. 29, 2016, 11 pages.
(Continued)

*Primary Examiner* — John P Leubecker
*Assistant Examiner* — Shankar Raj Ghimire
(74) *Attorney, Agent, or Firm* — Haynes and Boone, LLP (57) ABSTRACT

A medical device comprises an end effector for performing a medical procedure, a first connector, and a second connector. The first connector comprises a housing, a first interface, and a second interface. The first interface is coupled to the housing and includes a rod through which a first operational channel extends. The second interface is coupled to the housing and includes a second operational channel. The second connector comprises a housing, a first socket, and a second socket. The housing comprises a cavity bounded by an inner surface including a back surface. The first socket is sized and shaped to receive the rod; the second socket is sized and shaped to receive the second interface and projects from the back surface. The rod engages with the first socket to at least partially align the second interface with the second socket before the second interface engages with the second socket.

20 Claims, 13 Drawing Sheets

(51) Int. Cl.
*A61B 34/20* (2016.01)
*A61B 34/35* (2016.01)
*A61B 1/05* (2006.01)
*A61B 34/30* (2016.01)
*A61B 18/00* (2006.01)
*A61B 17/00* (2006.01)

(52) U.S. Cl.
CPC ............ *A61B 1/00128* (2013.01); *A61B 1/05* (2013.01); *A61B 34/20* (2016.02); *A61B 34/35* (2016.02); *A61B 34/70* (2016.02); *A61B 2017/00477* (2013.01); *A61B 2018/00172* (2013.01); *A61B 2018/00178* (2013.01); *A61B 2034/2065* (2016.02); *A61B 2034/301* (2016.02); *A61B 2034/306* (2016.02)

(58) Field of Classification Search
CPC ...... A61B 34/32; A61B 34/35; G02B 6/4292; G02B 6/4298
USPC ......... 439/909, 374, 526, 173, 246; 600/132
See application file for complete search history.

(56) References Cited

U.S. PATENT DOCUMENTS

| | | | |
|---|---|---|---|
| 4,611,887 A | 9/1986 | Glover et al. | |
| 5,039,456 A * | 8/1991 | Bowen | B29D 11/0075 264/1.25 |
| 5,239,983 A * | 8/1993 | Katsurada | A61B 1/00124 439/171 |
| 5,933,558 A * | 8/1999 | Sauvageau | G02B 6/4292 385/88 |
| 6,062,740 A * | 5/2000 | Ohtsuka | G02B 6/3833 385/77 |
| 6,350,160 B1 * | 2/2002 | Feuersanger | H01R 13/6456 439/680 |
| 6,371,663 B1 * | 4/2002 | Kneier | G02B 6/4246 385/88 |
| 6,374,004 B1 * | 4/2002 | Han | G02B 6/4206 385/14 |
| 6,547,454 B2 * | 4/2003 | Wickman | G02B 6/423 385/52 |
| 8,128,558 B2 * | 3/2012 | Amling | A61B 1/00119 385/75 |
| 8,187,015 B2 * | 5/2012 | Boyd | A61N 1/375 439/263 |
| 8,382,666 B1 * | 2/2013 | Mao | A61B 1/00121 600/202 |
| 8,757,893 B1 * | 6/2014 | Isenhour | G02B 6/3886 385/76 |
| 2002/0034363 A1 * | 3/2002 | Wickman | G02B 6/423 385/88 |
| 2004/0071407 A1 * | 4/2004 | Vergeest | G02B 6/3809 385/58 |
| 2004/0266257 A1 | 12/2004 | Ries et al. | |
| 2005/0282426 A1 * | 12/2005 | Nagashima | H01R 13/6315 439/374 |
| 2008/0188869 A1 * | 8/2008 | Weitzner | A61B 1/0014 606/130 |
| 2008/0287738 A1 * | 11/2008 | Adachi | A61B 1/00039 600/118 |
| 2010/0250000 A1 * | 9/2010 | Blumenkranz | A61B 34/30 700/258 |
| 2011/0071347 A1 * | 3/2011 | Rogers | A61B 1/00149 600/104 |
| 2011/0071541 A1 * | 3/2011 | Prisco | A61B 17/3421 606/130 |
| 2013/0184527 A1 * | 7/2013 | Castellucci | A61B 1/00135 600/121 |
| 2015/0342690 A1 * | 12/2015 | Zubiate | A61B 18/22 606/130 |
| 2016/0190739 A1 * | 6/2016 | Jiang | A61B 90/00 439/374 |

OTHER PUBLICATIONS

International Search Report and Written Opinion for Application No. PCT/US15/20879, dated Jul. 14, 2015, 14 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

MULTI-STAGE INSTRUMENT CONNECTOR

CROSS-REFERENCE TO RELATED APPLICATIONS

This application is the U.S. national phase of International Application No. PCT/US2015/020879, filed Mar. 17, 2015, which designated the U.S. and is related to and claims priority to U.S. Provisional Application No. 61/954,200 filed Mar. 17, 2014, entitled "MULTI-STAGE INSTRUMENT CONNECTOR" by Bruce M. Schena, the contents of which are incorporated herein by reference in their entirety and for all purposes.

FIELD

The present disclosure is directed to systems and methods for coupling surgical instruments to input/output sources, and more particularly to systems and methods for efficiently and reliably integrating making connections to surgical instruments.

BACKGROUND

Surgical instruments such as those used in minimally invasive medical procedures are intended to enhance the performance of such procedures and/or reduce the amount of tissue that is damaged, thereby reducing patient recovery time, discomfort, and deleterious side effects. Such instruments often require multiple input/output connections. For example, CCD endoscopes include connectors to for high-powered illumination sources and additional electrical connectors for the operation of the digital imaging electronics. However, the presence of multiple connectors can increase setup time and potentially increase the chance of connector damage.

Accordingly, it is desirable to provide a surgical instrument that facilitates quick and reliable connections.

SUMMARY

By integrating a first transmission channel for a surgical instrument into a connection alignment feature, a connector structure can be implemented that sequentially aligns and engages a second transmission channel after the first transmission channel.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the embodiments of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

As used herein, "end effector" may refer generally to a functional end of a medical device. For instance, one example of an end effector is a connector at the end of a length of cable. Another example of an end effector is an image capture device located at a distal end of an endoscope. "End effector" can also refer to an actual working distal part that is manipulable by means of a wrist member for a medical function, e.g., for effecting a predetermined diagnosis or treatment of a target tissue. For instance, some end effectors have a single working member such as an image capture device, a scalpel, a blade, or an electrode. Other end effectors have a pair or plurality of working members such as forceps, graspers, scissors, or clip appliers, for example. In certain embodiments, the disks or vertebrae are configured to have openings which collectively define a longitudinal lumen or space along the wrist, providing a conduit for any one of a number of alternative elements or instrumentalities associated with the operation of an end effector. Examples include conductors for electrically activated end effectors (e.g., electrosurgical electrodes; transducers, sensors, and the like); conduits for fluids, gases or solids (e.g., for suction, insufflation, irrigation, treatment fluids, accessory introduction, biopsy extraction and the like); mechanical elements for actuating moving end effector members (e.g., cables, flexible elements or articulated elements for operating grips, forceps, scissors); wave guides; sonic conduction elements; fiber optic elements; and the like. Such a longitudinal conduit may be provided with a liner, insulator or guide element such as a elastic polymer tube; spiral wire wound tube or the like.

As used herein, the terms "surgical instrument", "instrument", "surgical tool", or "tool" refer to a member having a working end which carries one or more end effectors to be introduced into a surgical site in a cavity of a patient, and is actuatable from outside the cavity to manipulate the end effector(s) for effecting a desired treatment or medical function of a target tissue in the surgical site. The instrument or tool typically includes a shaft carrying the end effector(s) at a distal end, and is preferably servomechanically actuated by a telesurgical system for performing functions such as holding or driving a needle, grasping a blood vessel, and dissecting tissue.

By integrating a first transmission channel for a surgical instrument into a connection alignment feature, a connector structure can be implemented that sequentially aligns and engages a second transmission channel after the first transmission channel.

Figure 1:
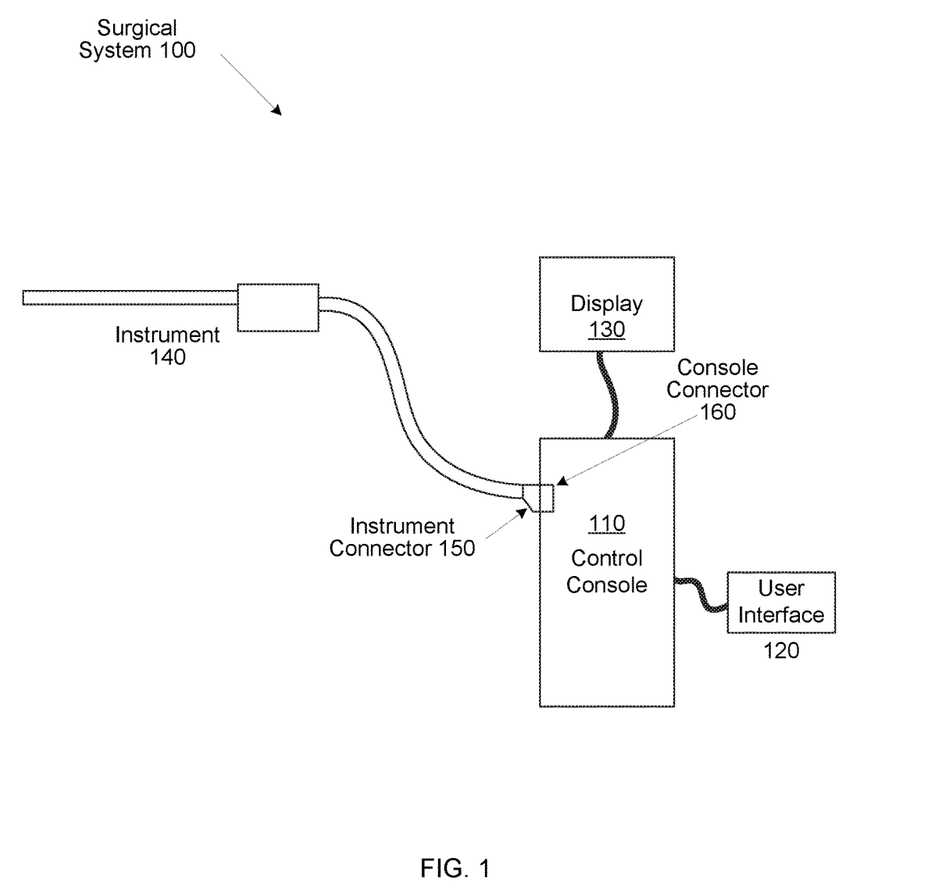
FIG. 1 shows an exemplary medical system including a multi-mode integrated connector.

Referring to FIG. 1 of the drawings, a surgical system is generally indicated by the reference numeral 100. Note that as used herein, "surgical" can refer to any medical procedure performed on a patient, including without limitation operative procedures (e.g., tissue extraction or manipulation), therapeutic procedures (e.g., medicament delivery), and diagnostic procedures (e.g., tissue examination or biopsy). As shown in FIG. 1, the surgical system 100 generally includes a control console 110 for operating a surgical instrument 140. A user interface 120 allows a clinician to operate/monitor instrument 140 (e.g., via an optional display 130). Such operation/monitoring can be direct or remote (e.g., teleoperated).

In some embodiments, user interface 120 will be provided with the same degrees of freedom as the associated surgical instrument 140 to provide the clinician with telepresence, or the perception that control interface(s) in user interface 120 are integral with instruments 140 so that the clinician has a strong sense of directly controlling instruments 140 (although in other embodiments, user interface 120 may have more or less degrees of freedom than surgical instrument 140). In some embodiments, the user interface 120 can include manual input devices which move with six degrees of freedom, and which may also include an actuatable handle for actuating instruments (for example, for closing grasping jaws, applying an electrical potential to an electrode, delivering a medicinal treatment, or the like). In other embodiments, user interface 120 can include switches, dials, or other adjustment interfaces to control the operational parameters of instrument 140.

Optional display 130 may display an image of the surgical site and surgical instruments captured by one or more imaging elements of system 100. In some embodiments, instrument 140 can include a camera system (e.g., an endoscope) to provide the imaging information. Alternatively or additionally, display 130 may present images of the surgical site recorded and/or modeled preoperatively and/or intraoperatively by an external imaging system that can use imaging technology such as, computerized tomography (CT), magnetic resonance imaging (MRI), positron emission tomography (PET), fluoroscopy, thermography, ultrasound, optical coherence tomography (OCT), thermal imaging, impedance imaging, laser imaging, or nanotube X-ray imaging, among others. The presented images may include two-dimensional, three-dimensional, or four-dimensional images. Note that as used herein, "external imaging" or "external image" refers to an image of the target anatomy taken from outside the patient, as opposed to "in-situ" images taken from within the patient, regardless of the specific imaging modality (e.g., ultrasound can be used for both external imaging and/or in-situ imaging).

In some embodiments, the display system 130 may alternatively or additionally display a virtual navigational image in which the actual location of the surgical instrument is registered (i.e., dynamically referenced) with preoperative or intraoperative images to present the clinician S with a virtual image of the internal surgical site at the location of the tip of the surgical instrument. An image of the tip of the surgical instrument or other graphical alphanumeric indicators may be superimposed on the virtual image to assist the clinician controlling the surgical instrument. Alternatively, the surgical instrument may not be visible in the virtual image.

In other embodiments, the display system 130 may alternatively or additionally display a virtual navigational image in which the actual location of the surgical instrument is registered with preoperative or concurrent intraoperative images to present the clinician with a virtual image of the surgical instrument within the surgical site from an external viewpoint. An image of a portion of the surgical instrument or other graphical or alphanumeric indicators may be superimposed on the virtual image to assist the clinician controlling the surgical instrument.

Instrument 140 includes an instrument connector 150 that mates with a console connector 160 on control console 110 to provide coupling between instrument 140 and control console 110. As shown in FIG. 1, instrument connector 150 and console connector 160 can be disengaged to disconnect instrument 140 from console 110. Instrument 140 includes a primary transmission channel 154 for a first mode of operative communication, and at least one secondary transmission channel 155 for a second mode of operative communication. Each mode of operative communication represents an operative input and/or output to instrument 140, such as data transmission, energy delivery, material delivery/removal, or any other type of interaction required by instrument 140 during use.

For illustrative purposes, instrument 140 is described below as an endoscope, which requires a first pathway for high intensity illumination (channel 154) and a second pathway for imaging controls/captured image data (channel 155). However, in various other embodiments, an endoscope might also include alternative or additional pathways for irrigation and/or suction. And in various other embodiments, instrument 140 can be any instrument that includes two or more discrete transmission channels, such as an ablation catheter with an RF energy input pathway and an irrigation pathway, or an electrosurgical dissection/coagulation tool having a fluid flow pathway and an electrical energization pathway, among others.

Instrument connector 150 includes a primary engagement feature 152 coupled to primary transmission channel 154, and a secondary engagement feature 153 coupled to secondary transmission channel 155. Console connector 160 includes a corresponding primary engagement feature 162 coupled to primary transmission channel 164 and a secondary engagement feature 163 coupled to secondary transmission channel 165. When instrument connector 150 and console connector 160 are mated, features 152 and 162 are engaged, and features 153 and 163 are engaged, thereby allowing transmission between instrument 140 and console 110 along primary transmission channels 154/164 and secondary transmission channels 155/165.

Figure 2:
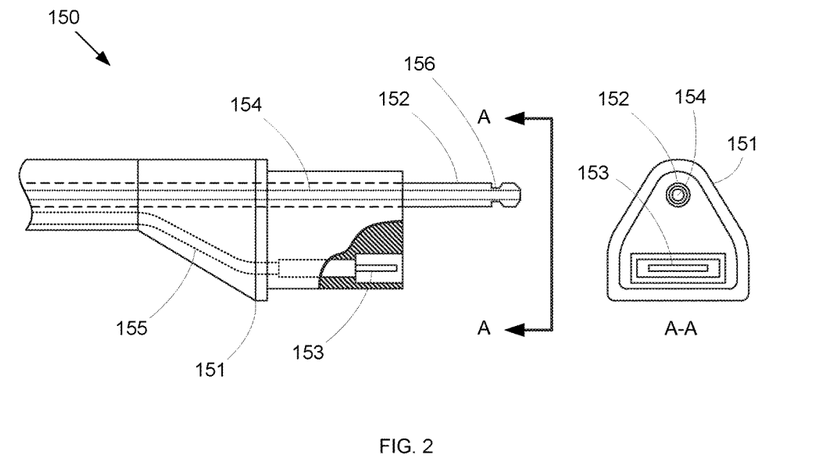
FIG. 2 shows an exemplary instrument connector incorporating multiple mode interfaces.

FIG. 2 shows an exemplary embodiment of instrument connector 150 that includes a connector housing 151 that contains primary engagement feature 152 and secondary engagement feature 153 for primary transmission channel 154 and secondary transmission channel 155, respectively, in instrument 140 (not shown for clarity). Primary engagement feature 152 can include an optional engagement lock 156 for establishing a fully connected condition, as described in greater detail below. While depicted and described herein as a basic groove for exemplary purposes, in various other embodiments, engagement lock can take any form (e.g., ridge(s), multiple grooves, flat face(s), clip-ring, etc.) and can be passive as shown or active (e.g., spring-loaded latch, clamp, etc.), and can be automatically or manually engaged and/or released.

As noted above, in various embodiments, instrument connector 150 can include multiple secondary engagement features 153 for multiple secondary transmission channels 155. Note further that while primary engagement feature 152 is depicted as a single cylindrical pin for exemplary purposes, in various other embodiments, primary engagement feature 152 can have any shape (e.g., non-circular pin, tapered pin, prismatic rod, sheath with or without additional interior elements, etc.) any quantity (e.g., multiple pins or other features). Likewise, while secondary engagement feature 153 is depicted as a rectangular protrusion within a slot for exemplary purposes, in various other embodiments, secondary engagement feature 153 can take any form (e.g., empty slot, socket, pins, etc.) and quantity. In addition, although housing 151 is depicted as a axially asymmetrical shape (pentagon) for exemplary purposes, in various other embodiments, housing 151 can take an shape (e.g., circular, square, rectangular, triangular, oval, etc.).

Figure 3:
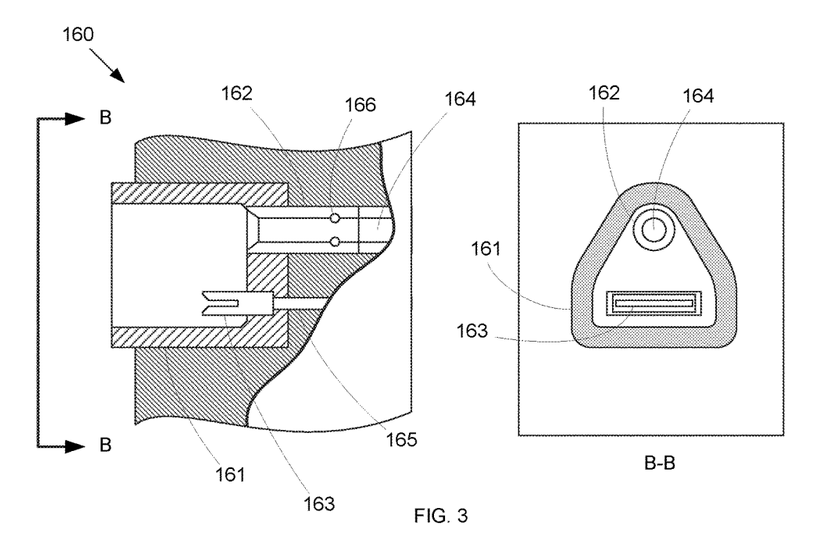
FIG. 3 shows an exemplary console connector incorporating multiple mode interfaces.

FIG. 3 shows an exemplary embodiment of console connector 160 that includes a connector housing 161 that contains primary engagement feature 162 and secondary engagement feature 163 for primary transmission channel 164 and secondary transmission channel 165, respectively, in console 110 (not shown for clarity). Primary engagement feature 162 can include an optional engagement lock 166 for establishing a fully connected condition, as described in greater detail below. While depicted and described herein as a compliant ridge (e.g., coil spring, o-ring, spring-loaded ball) for exemplary purposes, in various other embodiments, engagement lock 166 can take any form (e.g., clamp, latch, hook, etc.) and can be active as shown or passive (e.g., groove(s), slot(s), etc.), and can be automatically or manually engaged and/or released.

As noted above, in various embodiments, console connector 160 can include multiple secondary engagement features 163 for multiple secondary transmission channels 155. Note further that while primary engagement feature 162 is depicted as a single cylindrical socket for exemplary purposes, in various other embodiments, primary engagement feature 162 can have any shape (e.g., non-circular socket, tapered socket, prismatic socket, socket with or without additional interior elements, mating pins, etc.) any quantity (e.g., multiple sockets/pins or other features). Likewise, while secondary engagement feature 163 is depicted as a rectangular protruding slot for exemplary purposes, in various other embodiments, secondary engagement feature 163 can take any form (e.g., empty slot, socket, pins, etc.) and quantity. In addition, although housing 161 is depicted as a axially asymmetrical shape (pentagon) for exemplary purposes, in various other embodiments, housing 151 can take any shape (e.g., circular, square, rectangular, triangular, oval, etc.).

Figure 4A:
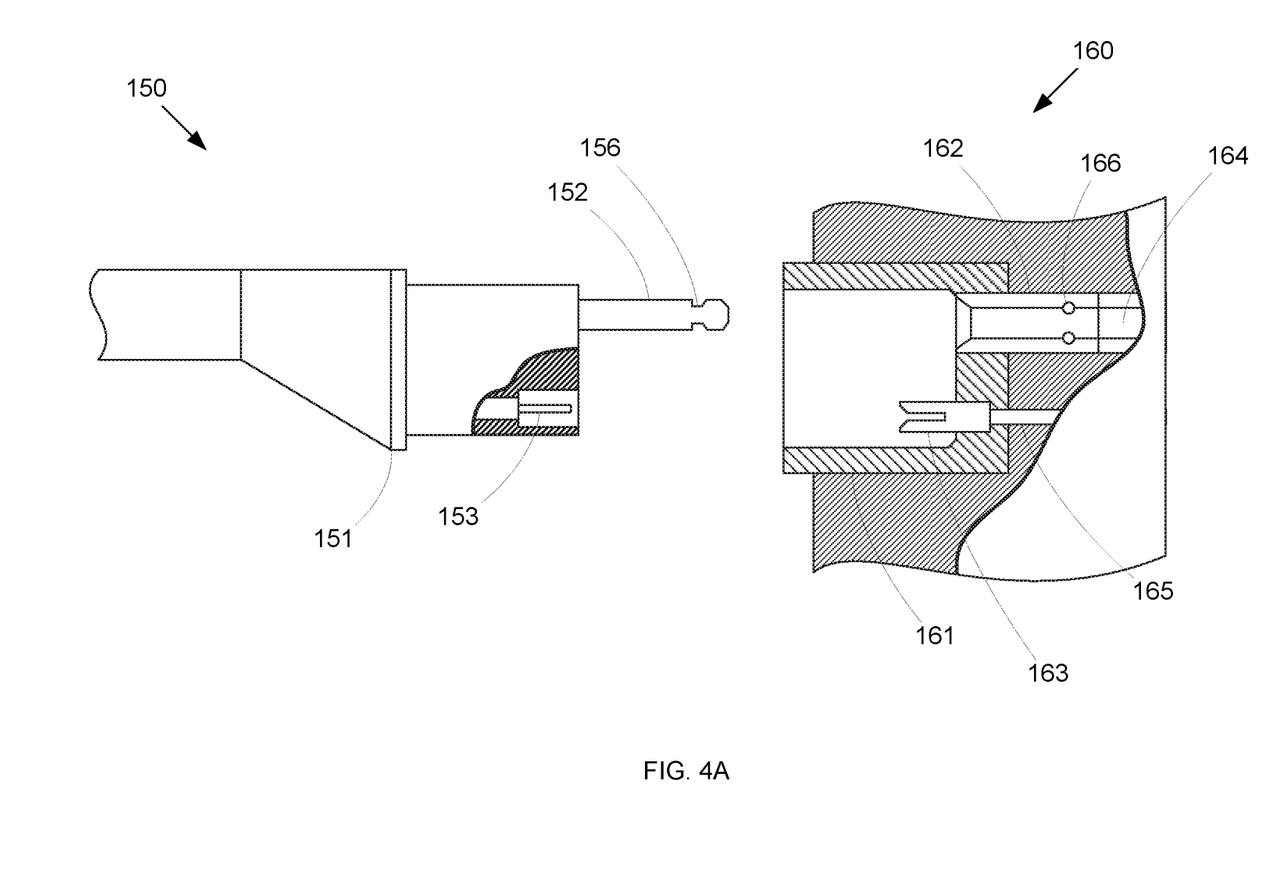
FIGS. 4A-4E show an exemplary engagement operation for the instrument connector of FIG. 2 and the console connector of FIG. 3.

FIGS. 4A-4E show an exemplary engagement operation between instrument connector 150 and console connector 160. In FIG. 4A, connectors 150 and 160 are positioned relative to one another in preparation for making a connection. Then in FIG. 4B, primary engagement feature 152 of instrument connector 150 begins to interact with console connector housing 161 as connectors 150 and 160 are moved towards each other. In this manner, primary engagement feature 152 establishes art initial relative positioning between connectors 150 and 160.

Figure 4B:
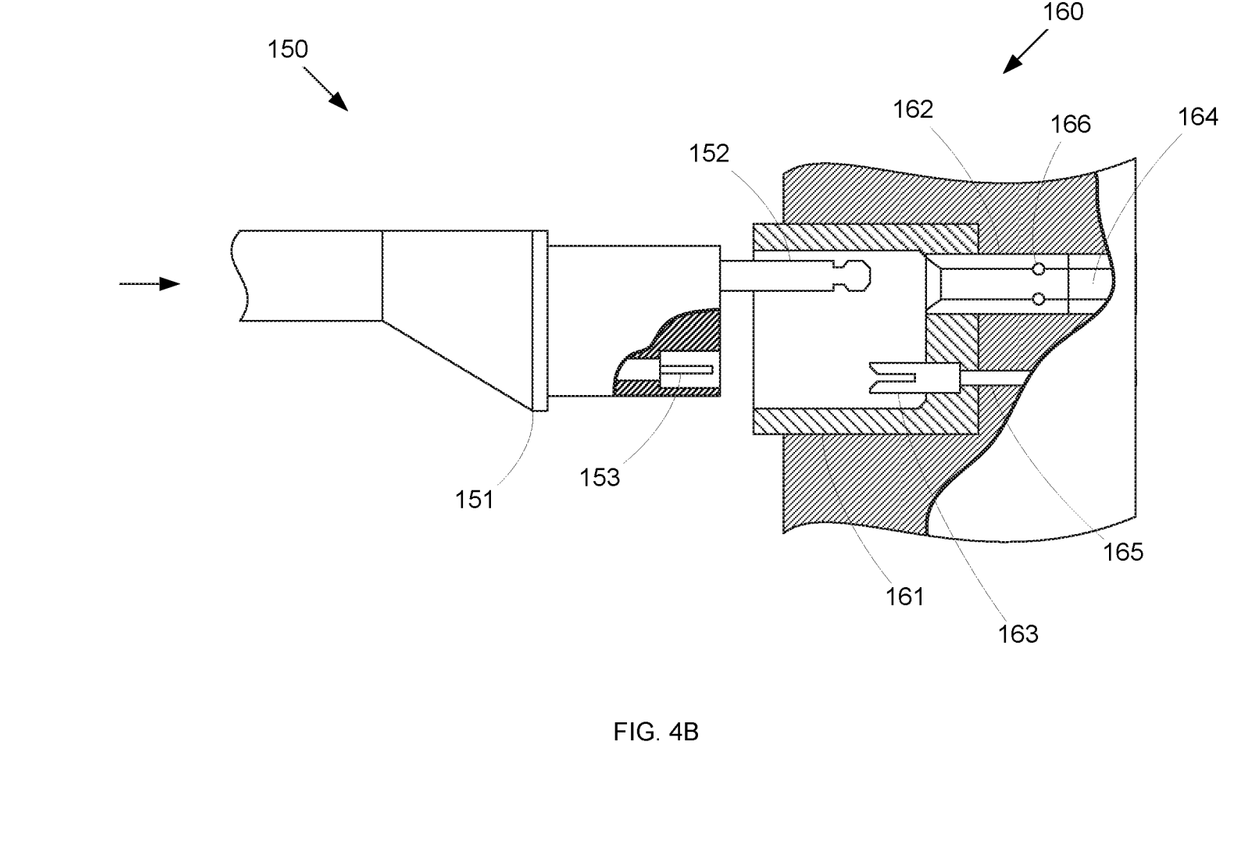
Figure 4C:
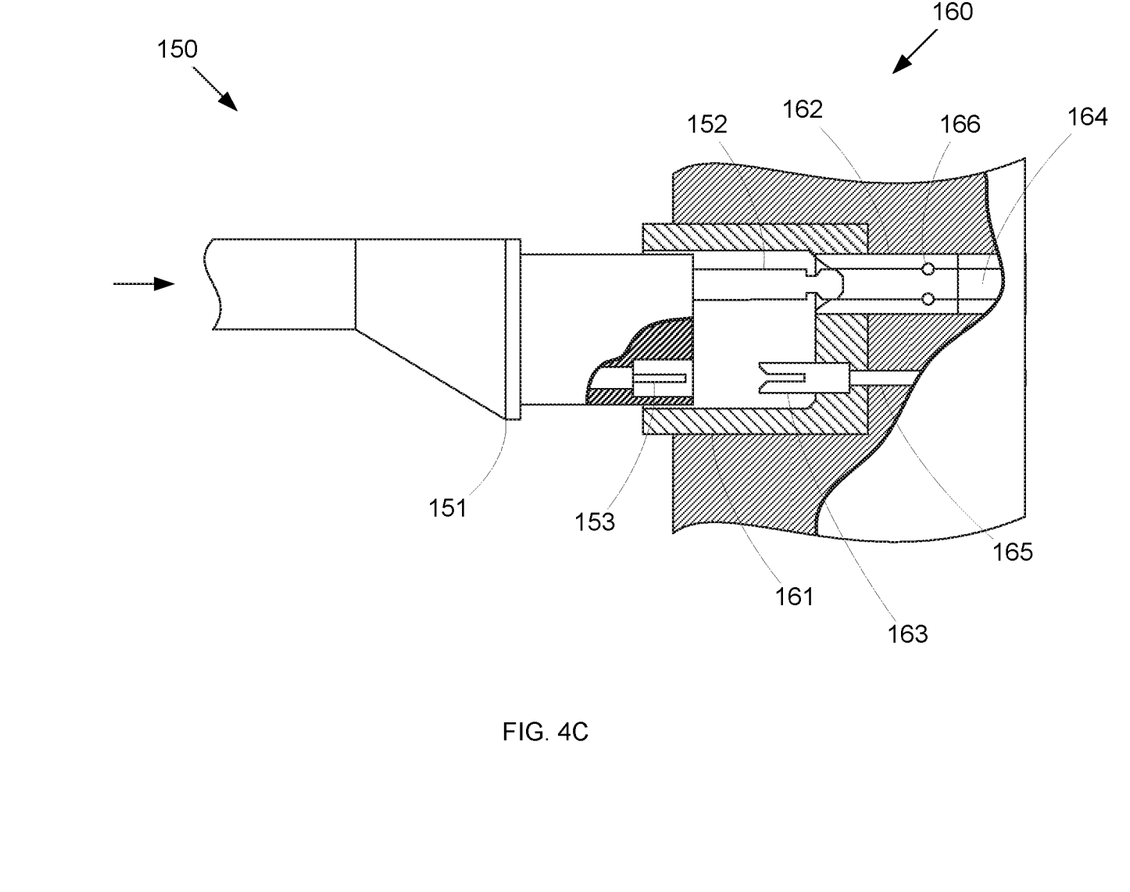

In some embodiments, primary engagement feature 152 can be a robust structural element that can be used for gross initial positioning movements with minimal risk of damage to itself, can also serve to minimize the risk of damage to secondary connector 153, and/or can provide precise relative positioning between secondary connectors 153 and 163 prior to engagement, as described in greater detail below. For example, in some embodiments, primary engagement feature 152 can be a metal (e.g., stainless steel) rod or tube, sized to mate with a corresponding metal socket in primary engagement feature 162 in connector 160.

In FIG. 4B, instrument connector housing 151 begins to interact with console connector housing 161. In some embodiments, where connector housing 151 and console housing 161 are axially asymmetrical (e.g., pentagonal shape as shown in FIGS. 2 and 3), this interaction can enforce a proper rotational orientation of instrument connector 150 with respect to console connector 160. In other embodiments, this rotational orientation can be established by an initial engagement of primary engagement feature 152 (e.g., if an axially asymmetrical pin, multiple pins, etc.) with primary engagement feature 162, or by separate orientation features (e.g., rails or slots on connector housings 151 and/or 161).

Figure 4D:
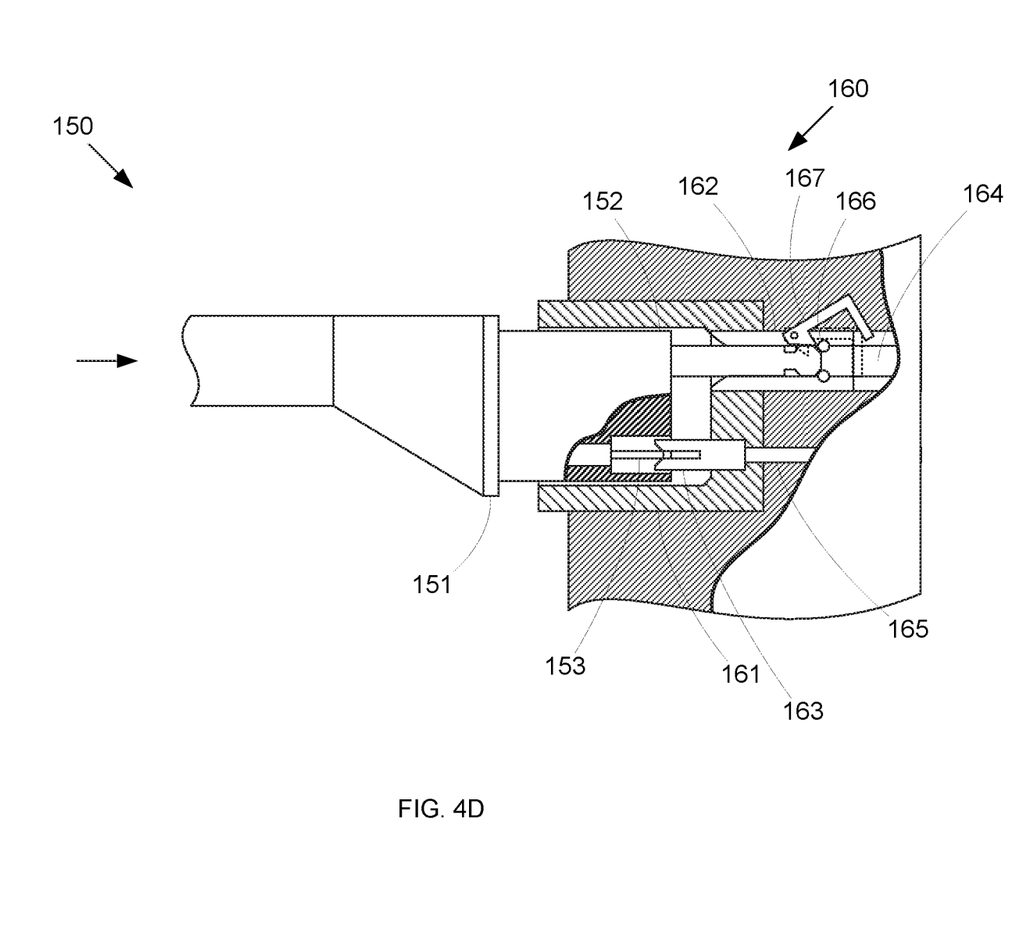

Primary engagement feature 152 also begins to engage with primary engagement feature 162. Features 152 and 162 can in various embodiments include chamfers, tapers, or any other features to assist in alignment as the features begin to interact with each other. Then, as shown in FIG. 4D, as primary engagement features 152 and 162 become increasingly mated, secondary engagement features 153 and 163 begin to engage, having been previously aligned by the mating of features 152 and 162 and optionally additionally by the mating of housings 151 and 161.

Figure 4E:
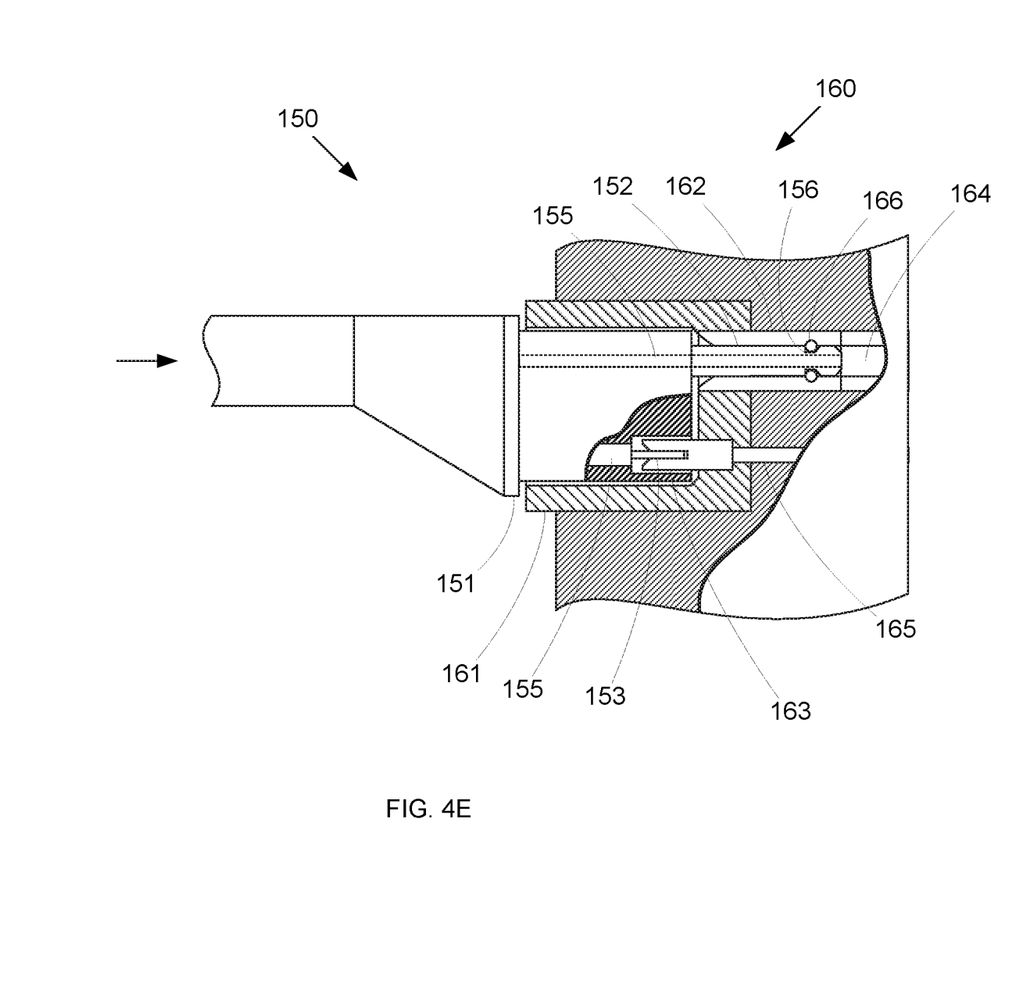

Finally, full engagement of connectors 150 and 160 is shown in FIG. 4E. As noted above, in some embodiments, primary engagement features 152 and 162 can optionally include locking features 156 and 166, respectively, that establish the final relative positioning of connectors 150 and 160. For example, locking feature 166 could be a canted coil spring, o-ring, expanding clip, or any other compliant or movable element/feature mounted in engagement feature 162 that nests into a groove corresponding to locking feature 156 when proper connector mating is achieved, and prevents further insertion to prevent damage to either connector. However, in various other embodiments, full engagement of the connectors could be established by opposing faces of housings 151 and 161, by secondary engagement features 153/163, or by any other means.

Thus, by establishing an accurate alignment of connector 150 with connector 160, primary engagement features 152 and 162 and/or connector housings 151 and 162 ensure that secondary engagement features 153 and 163 can be accurately engaged with minimal risk of damage. This can be particularly beneficial where secondary engagement features 153 and/or 163 are delicate or difficult/costly to replace (e.g., electrical connectors for imaging or sensor data transmission).

For example, an endoscope requires both a high intensity illumination light input and an electrical signal input/output for imaging controls and data. A bundle of optical fibers are often used to transport the illumination light from the light source to the distal tip of the endoscope. In some embodiments, primary engagement feature 162 in console connector 160 can be coupled to the transmission channel (164) from this high intensity light source, and primary engagement feature 152 in instrument connector 150 can be coupled to the transmission channel (155) that conveys the light to the endoscope tip. In such a construction, the rigidity and robustness of primary engagement feature 152 can provide the additional benefit of precisely controlling the alignment of the source transmission channel (164) with the instrument transmission channel (154), which can have a significant effect on lighting efficiency. Other types of transmission channels requiring precision alignment for proper communication across the connection (e.g., optical fiber connections for shape or force sensing, precision coaxial connectors, etc.) can similarly benefit from integration into the engagement feature itself.

In some embodiments, primary engagement features 152 and 162 and/or secondary engagement features 153 and 163 can include safety mechanisms to prevent inadvertent discharge from any of the transmission channels. For example, FIG. 4D shows an optional shutter mechanism 167 (e.g., a pivoting panel, expanding iris, or any other movable cover) mounted on primary engagement feature 162 in console connector 160. Shutter mechanism 167 is normally closed, thereby blocking any undesirable discharge from transmission channel 164 (for example, high intensity laser illumination light or electrical power). As engagement feature 152 mates with engagement feature 162, shutter mechanism 167 is moved out of the way once a safe degree of engagement is achieved to allow the operational coupling of transmission channels 154 and 164.

Figure 5A:
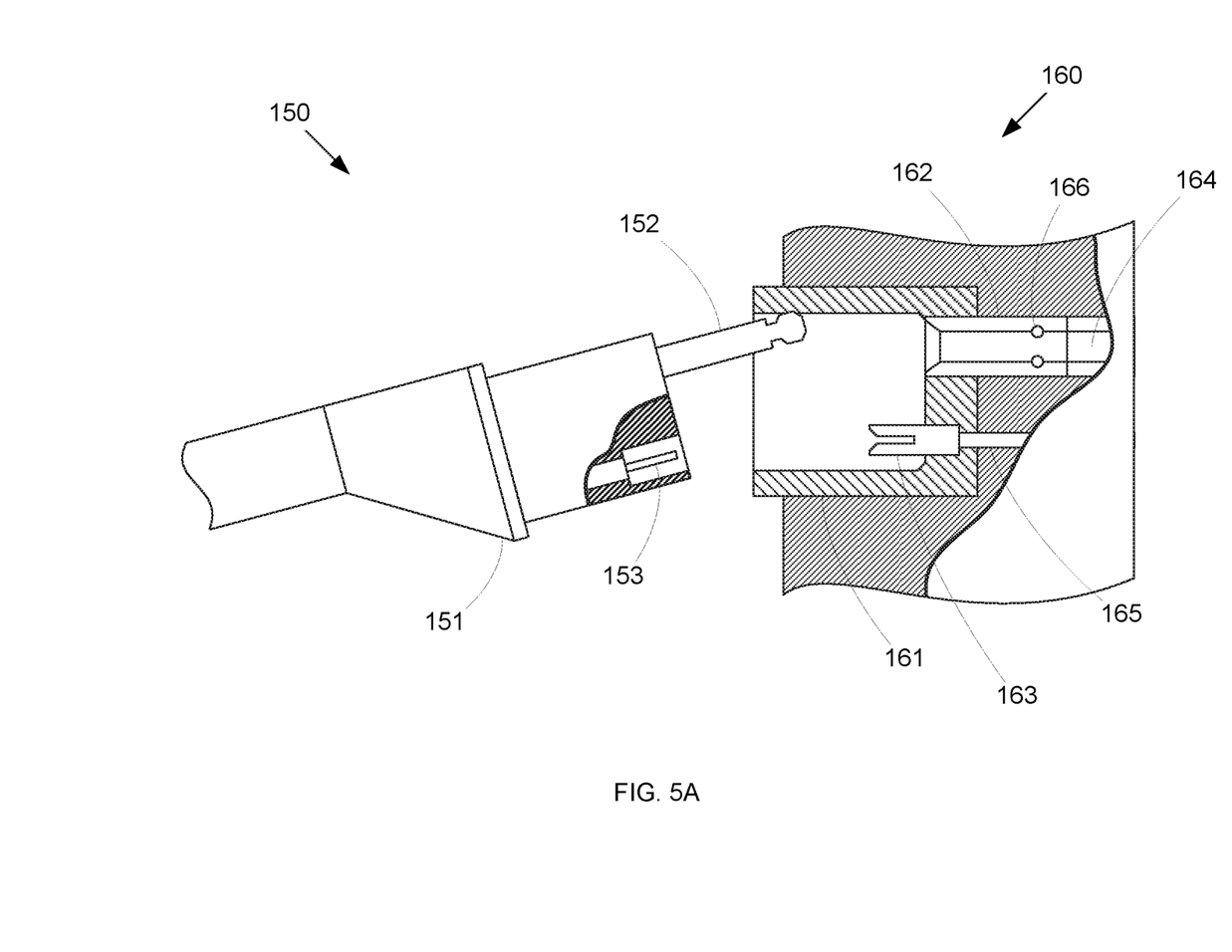
FIGS. 5A-5C show an exemplary engagement operation for an instrument connector and a console connector according to some embodiments.
Figure 5B:
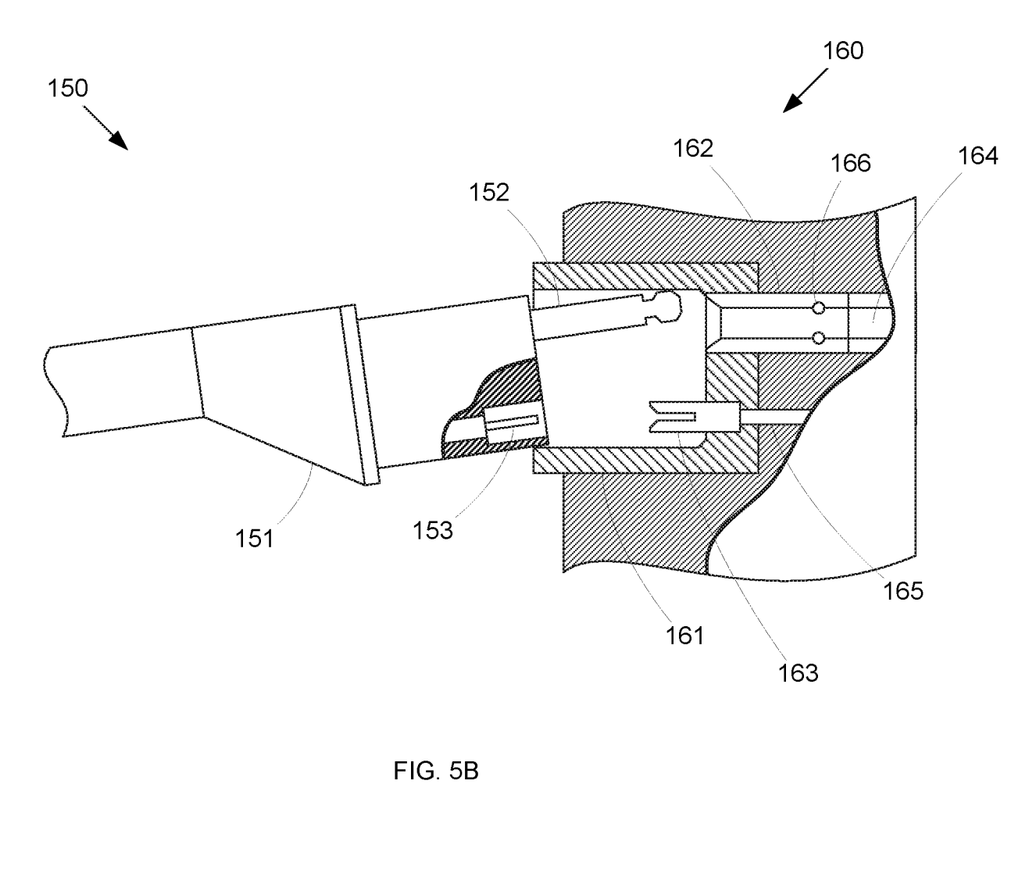
Figure 5C:
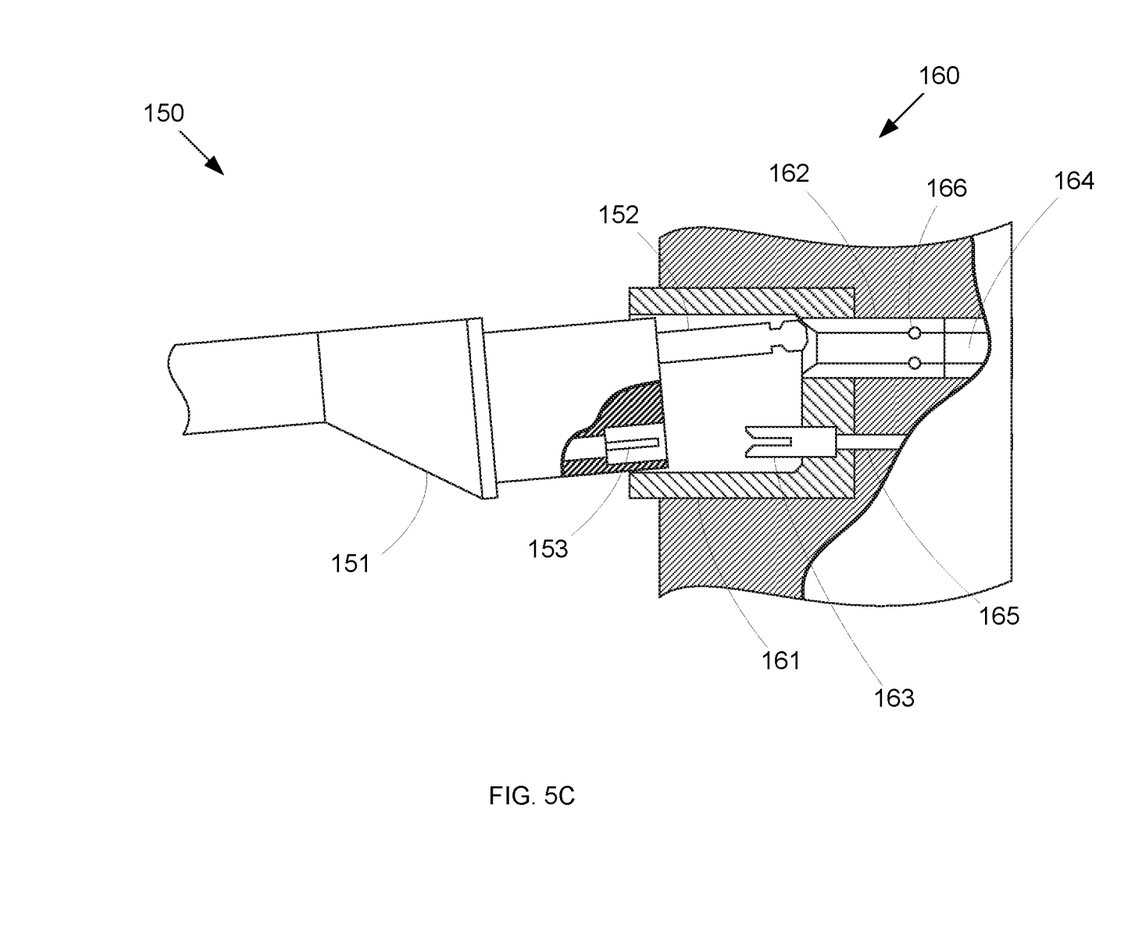

In some embodiments, primary engagement feature 152 and/or housing 151 can further ensure proper connector engagement when instrument connector 150 and console connector 160 are not properly aligned. For example, FIG. 5A shows connector 150 angled upwards with respect to connector 160. However, the initial interaction of primary engagement feature 152 with housing 161 tends to straighten connector 150 with respect to connector 160, as shown in FIG. 5B. Continued advancement further aligns connectors 150 and 160, so that eventually primary engagement feature 152 can begin to properly mate with primary engagement feature 162, as shown in FIG. 5C. The connection can then be completed as described above with respect to FIGS. 4C-4E.

Figure 6A:
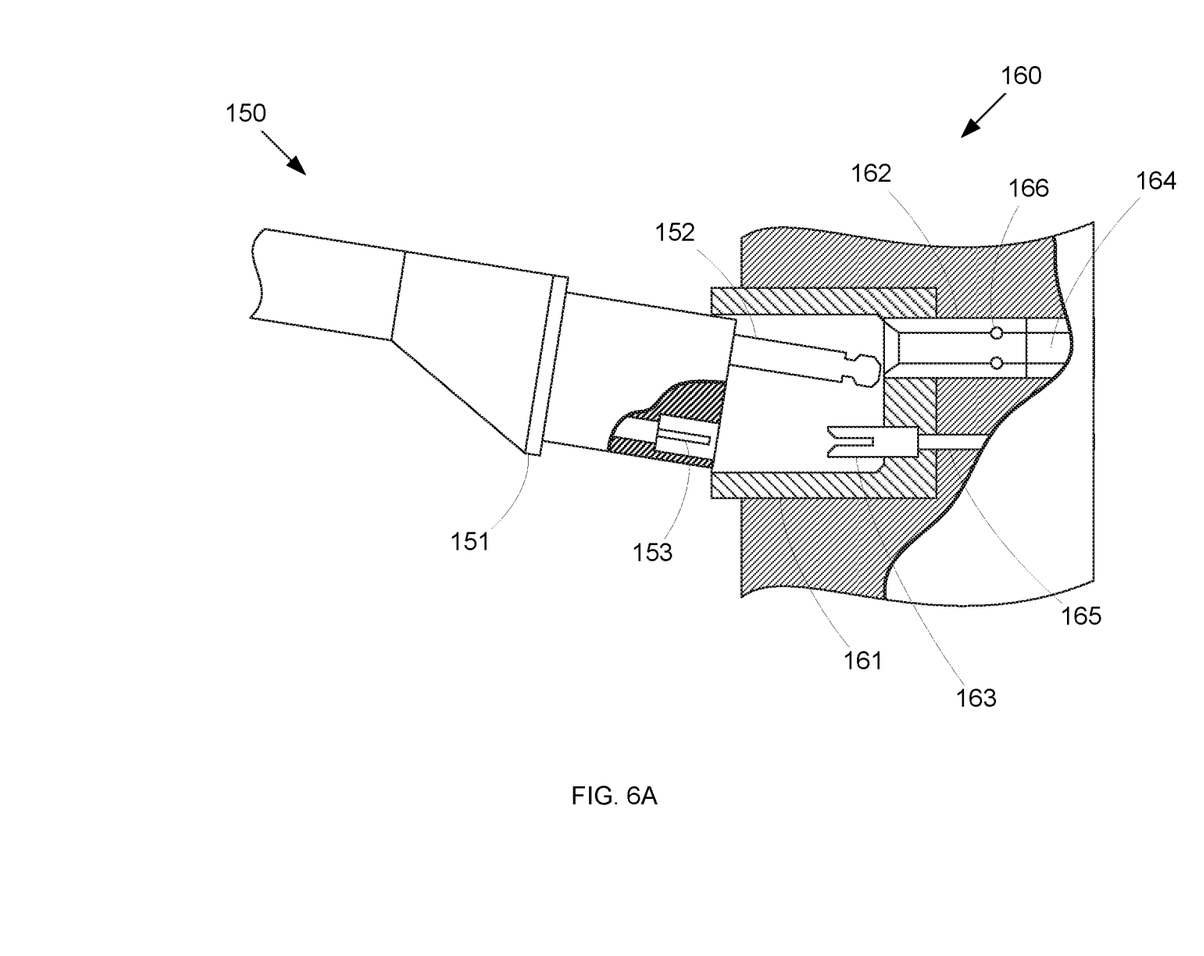
FIGS. 6A-6B show another exemplary engagement operation for the instrument connector of FIG. 2 and the console connector of FIG. 3.
Figure 6B:
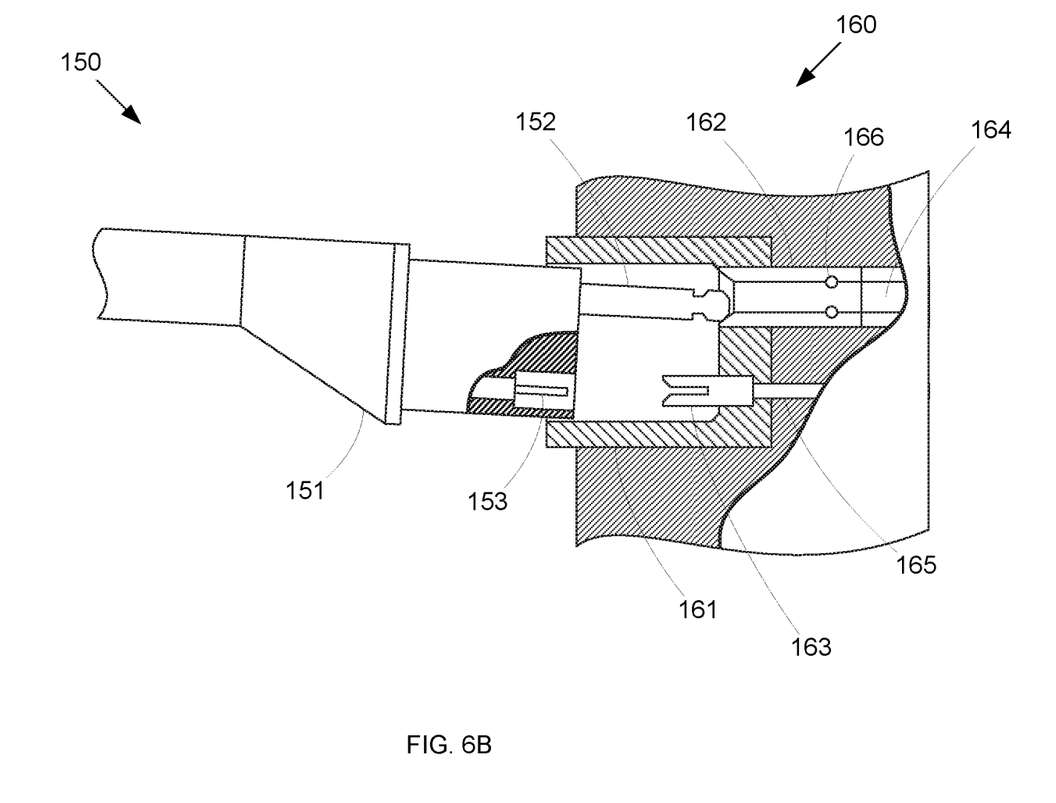

Similarly, FIG. 6A shows connector 150 angled downwards with respect to connector 160. Housing 151 is shaped and sized such that as connector 150 is aligned with connector 160 as it is further advanced towards connector 160, as shown in FIG. 6B. This also aligns primary engagement feature 152 with primary engagement feature 162, thereby allowing completion of the connection as described above with respect to FIGS. 4C-4E.

Figure 7:
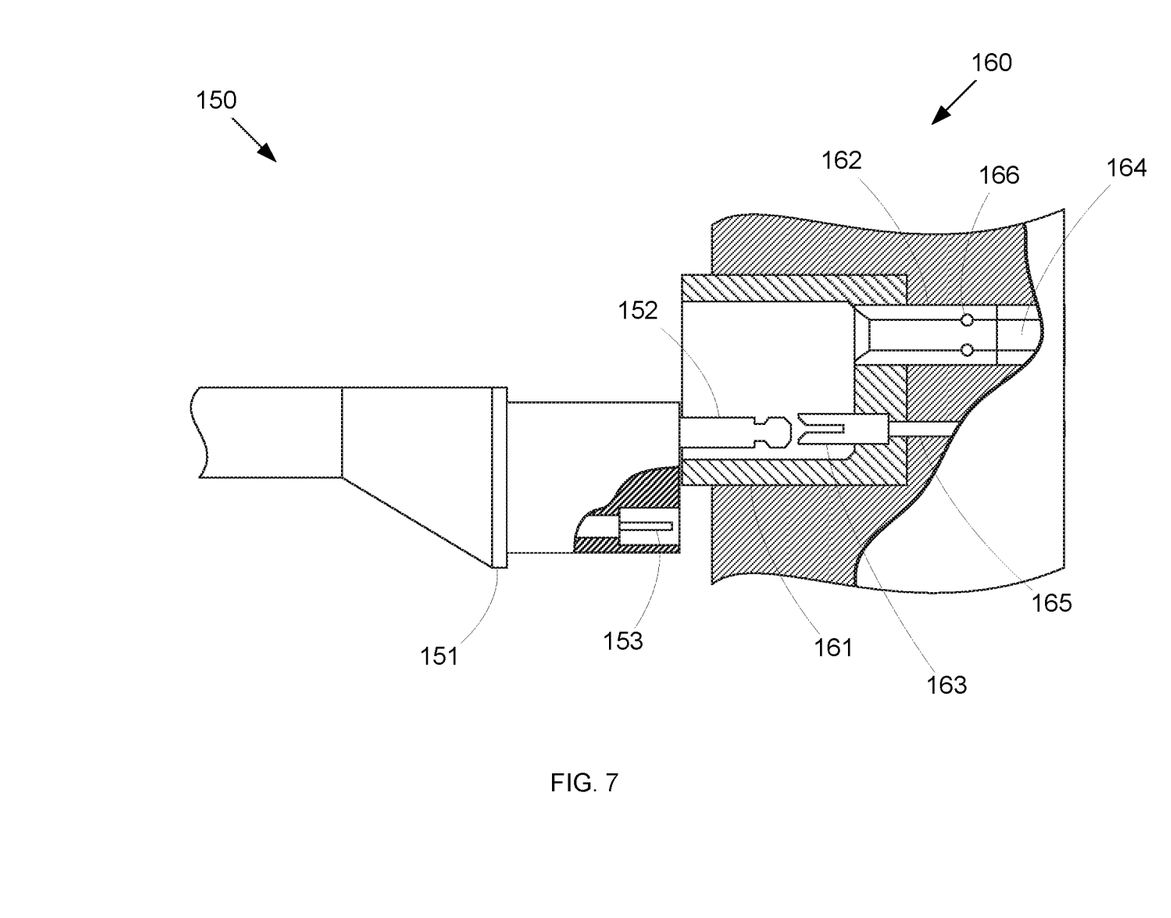
FIG. 7 shows an exemplary interaction between the instrument connector of FIG. 2 and the console connector of FIG. 3.

In various other embodiments, the robustness and reliability of the connection can be further enhanced by sizing/shaping primary engagement features 152/162, secondary engagement features 153/163, and/or housings 151/161 to ensure that potentially damaging contact cannot be made between the various engagement features. For example, as shown in FIG. 7, primary engagement feature 152 of instrument connector 150 can be sized such that it cannot contact secondary engagement feature 163 of console connector 160. In the exemplary depiction of FIG. 7, primary engagement feature 152 extends a distance from the outer face of connector housing 151 that is less than the depth at which secondary engagement feature 163 is recessed from the outer face of connector housing 161. However, various other housing/feature configurations could be implemented to provide a similar degree of enforced separation, such as sizing console housing 161 around secondary engagement feature 163 such that primary engagement feature 152 cannot fit within the access space (e.g., an opening smaller than or non-congruent with the cross-sectional shape of engagement feature 152).

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical device comprising:
   an end effector for performing a medical procedure;
   a first connector comprising:
      a housing;
      a first interface for a first operational channel for the end effector, the first interface coupled to the housing of the first connector and including a rod through which the first operational channel extends; and
      a second interface for a second operational channel for the end effector, the second interface coupled to the housing of the first connector; and
   a second connector comprising:
      a housing comprising a cavity bounded by an inner surface including a back surface;
      a first socket sized and shaped to receive the rod; and
      a second socket sized and shaped to receive the second interface, the second socket projecting from the back surface into the cavity,
   wherein the rod is configured to engage with the inner surface of the housing of the second connector before the rod engages with the first socket,
   wherein at least a portion of the housing of the first connector is configured to extend within the housing of the second connector before the second interface engages with the second socket,
   wherein the rod is configured to engage with the first socket to at least partially align the second interface with the second socket before the second interface engages with the second socket, and
   wherein the first socket manipulates the rod from a non-aligned position to an aligned position during advancement of the rod toward the first socket.

2. The medical device of claim 1, wherein the first operational channel comprises one or more fiber optic elements, and wherein the second operational channel comprises an electrical pathway.

3. The medical device of claim 2, wherein the one or more fiber optic elements are configured to convey illumination light.

4. The medical device of claim 3, further comprising a camera system for capturing image data and transmitting the image data along the electrical pathway.

5. The medical device of claim 2, wherein the one or more fiber optic elements comprise optical fiber connections for at least one of shape sensing or force sensing.

6. The medical device of claim 2, wherein the rod at least partially surrounds at least a portion of the one or more fiber optic elements.

7. The medical device of claim 6, wherein the rod comprises one or more locking elements.

8. The medical device of claim 1, wherein the rod comprises a metal pin.

9. The medical device of claim 1, wherein the second interface is embedded within the housing of the first connector.

10. A surgical instrument console comprising:
    a high-intensity illumination light source;

a transmitter configured to transmit at least one of image data or sensor data;
a first connector comprising:
  a housing comprising a cavity bounded by an inner surface including a back surface;
  a first socket for coupling to the high-intensity illumination light source; and
  a second socket for coupling to the transmitter, the second socket projecting from the back surface into the cavity; and
a mating connector comprising:
  a housing;
  a first interface including a rod, the rod coupled to the housing of the mating connector, the rod sized and shaped to fit within the first socket; and
  a second interface coupled to the housing of the mating connector, the second interface sized and shaped to fit within the second socket,
wherein the rod is configured to engage with the inner surface of the housing of the first connector before the rod engages with the first socket,
wherein at least a portion of the housing of the mating connector is configured to extend within the housing of the first connector before the second interface contacts the second socket,
wherein the first socket is configured to mate with the rod to align the second interface with the second socket before the second interface contacts the second socket, and
wherein the first socket manipulates the rod from a non-aligned position to an aligned position during advancement of the rod toward the first socket.

11. The surgical instrument console of claim 10, wherein the first socket comprises a shutter that obstructs the high-intensity illumination light source when the first socket is not mated with the rod.

12. The surgical instrument console of claim 10, wherein the high-intensity illumination light source is coupled to one or more fiber optic elements that comprise optical fiber connections for at least one of shape sensing or force sensing.

13. The surgical instrument console of claim 10, wherein the high-intensity illumination light source is coupled to one or more fiber optic elements for transmitting illumination light.

14. The surgical instrument console of claim 10, wherein the rod at least partially surrounds at least one optical fiber.

15. The surgical instrument console of claim 14, wherein the high-intensity illumination light source is coupled to one or more fiber optic elements, wherein:
  the one or more fiber optic elements comprise optical fiber connections for at least one of shape sensing or force sensing, and
  the one or more fiber optic elements transmit illumination light.

16. The surgical instrument console of claim 10, wherein the first socket comprises at least one locking element for establishing a fully engaged configuration with the rod.

17. The surgical instrument console of claim 10, wherein the first socket further comprises a transmission channel that couples the first socket to the high-intensity illumination light source.

18. The surgical instrument console of claim 17, wherein the rod further comprises a transmission channel, and wherein the transmission channel of the first socket is configured to align with the transmission channel of the rod when the first socket is mated with the rod.

19. The surgical instrument console of claim 10, wherein:
  the rod comprises a metal pin; and
  the first socket comprises a metal socket.

20. The surgical instrument console of claim 10, wherein the second interface is embedded within the housing of the mating connector.

* * * * *